United States Patent

Raheja et al.

[11] Patent Number: 5,320,843
[45] Date of Patent: Jun. 14, 1994

[54] METHOD FOR IMPROVING ANTIBACTERIAL PROPERTIES OF OPHTHALMIC SOLUTIONS

[75] Inventors: Manohar K. Raheja, North Andover; Stanley J. Wrobel, Andover, both of Mass.

[73] Assignee: Polymer Technology Corporation, Wilmington, Mass.

[21] Appl. No.: 988,649

[22] Filed: Dec. 10, 1992

[51] Int. Cl.$^5$ ............................. A61K 9/00; A61K 9/66
[52] U.S. Cl. ..................................... 424/405; 206/5.1; 206/438; 206/524.4; 424/618; 424/682; 424/684; 424/630; 424/641; 514/772.3
[58] Field of Search .................. 206/524.4, 438, 5.1; 514/772.3; 424/684, 682, 618, 630, 641

[56] References Cited

U.S. PATENT DOCUMENTS

| | | | |
|---|---|---|---|
| 4,525,410 | 6/1985 | Hagiwara et al. | 428/198 |
| 4,775,585 | 10/1988 | Hagiwara et al. | 428/323 |
| 4,906,464 | 3/1990 | Yamamoto et al. | 424/78 |
| 4,911,898 | 3/1990 | Hagiwara et al. | 423/118 |
| 4,911,899 | 3/1990 | Hagiwara et al. | 423/118 |
| 4,938,955 | 7/1990 | Niira et al. | 424/79 |
| 4,938,958 | 7/1990 | Niira et al. | 424/79 |
| 4,959,268 | 9/1990 | Hagiwara et al. | 428/403 |
| 5,003,638 | 4/1991 | Miyake et al. | 2/167 |
| 5,064,599 | 11/1991 | Ando et al. | 264/237 |
| 5,085,416 | 2/1992 | Miyake et al. | 269/289 |
| 5,154,325 | 10/1992 | Ryder et al. | 222/189 |

FOREIGN PATENT DOCUMENTS

| | | | |
|---|---|---|---|
| 0049767 | 4/1982 | European Pat. Off. | 206/5.1 |
| 0322171 | 6/1989 | European Pat. Off. | 206/524.4 |
| 2-080442 | 3/1990 | Japan . | |
| 2-125717 | 5/1990 | Japan . | |
| 4-022361 | 1/1992 | Japan . | |

OTHER PUBLICATIONS

H. Schweisfurth, B. Wunn: "Silver as an Agent for Storage and Disinfection of Contact Lenses", Contactologia 7 D (1985), pp. 144–147.

Apacider: A New Antimicrobial Additive, SGA Technical Bulletin.

Apacider ™, A New Patented Anti-Microbial Additive Suitable for Plastics, Filters, Paper and Coatings SGA.

A Sodium Silver Chloride Complex (SoluSept, Similasan AG, Switzerland), Executive Summary, pp. 1–4.

N. Kamikaidou et al., Chemical Abstract 117:66403z.

*Primary Examiner*—Thurman K. Page
*Assistant Examiner*—P. Kulkosky
*Attorney, Agent, or Firm*—John E. Thomas

[57] ABSTRACT

A method for improving the antibacterial efficacy of an ophthalmic solution, particularly a solution for the care of contact lenses, comprises providing an article molded from a plastic resin including an inorganic carrier retaining antibacterial metal ions, and placing the ophthalmic solution in contact with the plastic resin.

20 Claims, No Drawings

METHOD FOR IMPROVING ANTIBACTERIAL PROPERTIES OF OPHTHALMIC SOLUTIONS

BACKGROUND OF THE INVENTION

1. Field of the Invention

This invention relates to a method for improving the antibacterial efficacy of an ophthalmic solution, such as a solution used for the care of contact lenses. The solutions are contacted with a resin including antibacterial metal ions in an inorganic carrier.

2. Description of the Art

The majority of commercial ophthalmic solutions, including solutions used for the care of contact lenses, are packaged in dispensing bottles molded from a thermoplastic or thermosetting resin. Such solutions include saline solutions, cleaning solutions which incorporate a cleaning agent and conditioning solutions. Since these solutions come into direct contact with contact lenses or the eye, depending on the intended use of the solution, it is important that the solutions do not become contaminated with microorganisms such as bacteria. The current approach to avoid contamination of the solution involves packaging the solutions under sterile conditions and designing the container to minimize the likelihood of contamination from handling the container. Additionally, many solutions incorporate preservatives to inhibit growth of any microorganisms which may contaminate the solution.

Additionally, contact lens cases designed for storage of contact lenses or for care regimen of the lenses are generally constructed of a thermoplastic or thermosetting resin. When a contact lens is placed in a contact lens cell of the case, it is immersed in a solution. The current approach to inhibit microbial growth in the contact lens cells is to avoid contamination of the case to the extent possible, to cap the cell during use, and to rinse the case between uses. Microbial growth may also be inhibited by the solution placed in the contact lens cell.

It is known that silver ions may be incorporated in ophthalmic solutions to inhibit bacterial or microbial growth. For example, R. Schweisfurth et al. (*Contactologia*, Vol. 7 D (1985), pages 144-147) disclose antibacterial properties of silver as an agent for storage and disinfection of contact lenses. Additionally, a sodium silver chloride complex (SoluSept TM, Similasan AG, Switzerland) is described as a preservative for ophthalmic solutions.

Additionally, various agents having antibacterial or antimicrobial properties are known, including agents which can be incorporated in polymer resins, including films, fibers and molded articles. The following patent publications disclose antibacterial zeolites retaining at least one metal ion having antibacterial properties, such as ions of Ag, Cu or Zn, and various polymer articles having antibacterial properties which contain the zeolite: U.S. Pat. No. 4,525,410; U.S. Pat. No. 4,775,585; U.S. Pat. No. 4,906,464; U.S. Pat. No. 4,911,898; U.S. Pat. No. 4,911,899; U.S. Pat. No. 4,938,955; U.S. Pat. No. 4,938,958; U.S. Pat. No. 5,003,638; U.S. Pat. No. 5,064,599; U.S. Pat. No. 5,085,416; abstract of Japan 02/080,442; and abstract of Japan 02/125,717. Other materials which can retain antibacterial metal ions include amorphous aluminosilicate particles, disclosed in U.S. Pat. No. 4,959,268, and hydroxyapatite, such as Apacider TM (Sangi Group America Corp., Los Angeles). None of these references suggests the use of the antibacterial agents to improve the efficacy of an ophthalmic solution.

SUMMARY OF THE INVENTION

The invention relates to a method for improving the antibacterial efficacy of an ophthalmic solution, particularly a solution for the care of contact lenses. The method comprises providing an article molded from a plastic resin including an inorganic carrier retaining antibacterial metal ions, and placing the ophthalmic solution in contact with the article. The antibacterial metal ions leach from the resin to the ophthalmic solution.

DETAILED DESCRIPTION OF THE INVENTION

This invention relates to a method for improving the antibacterial efficacy of an ophthalmic solution. Preferred solutions include those used for the care of contact lenses, such as saline solutions, conditioning solutions, cleaning solutions, and wetting solutions. The solutions may be sterile, unpreserved solutions, or the solutions may contain a preservative which inhibits microbial growth, including bacterial growth. Thus, it is understood that the term "improve the antibacterial efficacy" includes imparting antibacterial properties to a solution, such as solutions which contain no preservatives or other antibacterial agents, as well as enhancing antibacterial properties of a solution which already contains an antibacterial component. Additionally, it is understood that the term "antibacterial" denotes an ability to kill or suppress the growth of bacteria, although the antibacterial agents employed in the methods of this invention will normally kill or suppress the growth of other microorganisms as well.

The antibacterial efficacy of the solution is improved by contacting the solution with the article composed of a plastic resin having incorporated therein antibacterial metal ions retained in an inorganic carrier. Preferred articles are containers generally used for contact lens care solutions, particularly containers having the form of a solution dispensing bottle or a contact lens case. Additionally, the article may be a plastic substrate for insertion in solution dispensing bottles such that the solution contained in the bottle contacts the plastic substrate.

Metal ions having antibacterial activity include ions of silver, copper, zinc, mercury, tin, lead, bismuth, cadmium, chromium and thallium. Silver ions, copper ions and zinc ions are especially preferred as ophthalmically acceptable metal ions. It has been found that inorganic carriers which retain antibacterial metal ions provide advantages over various other conventional antibacterial agents. First, the inorganic carriers can be readily incorporated in a plastic resin, and the resultant mixture can be processed into containers by conventional molding techniques. Additionally, it has been determined that the inorganic carrier and resin can be selected such that the metal ions leach from the resin to the solution. Since the metal ions leach out of the resin, solution dispensing bottles can be shipped or stored prior to packaging, and contact lens cases can be shipped or stored prior to initial use, without significant loss of the metal ions. Additionally, it is contemplated that contact lens cases can be reused until the resin is depleted of metal ions.

Although ophthalmic solution dispensing bottles are designed to minimize the likelihood of contamination by misuse, the method of the present invention provides for antibacterial effects should contamination occur, which is especially important for unpreserved solutions. The method is particularly useful for contact lens cases since the prevention of bacterial contamination is more dependent on the user following care regimen instructions. For example, a user may fail to properly clean the lens case between uses, and if the case becomes contaminated, a biofilm can then form on the surfaces of the case from colonization of the contaminating microorganisms. Such a biofilm provides means for bacteria to survive even when later subjected to a preserved solution since the biofilm "protects" microorganisms from contacting the solution. The invention provides a method of inhibiting the formation of such a biofilm on the surfaces of the contact lens case to further enhance the efficacy of an ophthalmic solution when placed in contact therewith.

The forms of solution dispensing bottles and contact lens cases are well known in the art. For example, solution dispensing bottles generally comprise a molded substantially cylindrical shell (including oval shaped shells) having a bottom and a nozzle and a sealable cap at its top. Contact lens cases generally comprise a molded body including at least one contact lens cell, and usually two cells, wherein each cell includes a cavity sized to hold a contact lens immersed in solution, and a sealable cap for the open upper end of the cavity.

The plastic resin is preferably a thermoplastic or thermosetting resin suitable for molding, such as injection molding or blow molding. Additionally, the resin is selected such that it is compatible with the inorganic carrier retaining the antibacterial metal ions. One class of resins are thermoplastic polyolefin resins, including high density polyethylene, low density polyethylene and polypropylene. Other resins include polycarbonates, polyvinyl chlorides, polystyrene, as well as other plastic resins known in the art.

The inorganic carrier must be one that retains the antibacterial metal ions and which is suitable for molding processes when combined with the plastic resin. Particularly, it is desirable that when the ophthalmic solution is in contact with the plastic resin, only the metal ions leach in the solution while the inorganic carrier remains in the resin.

A preferred inorganic carrier is a zeolite. Zeolites may be defined as a silicate of aluminum and a metal oxide having a three-dimensional skeletal structure, and represented by the formula $XM_{2/n}O \cdot Al_2O_3 \cdot YSiO_2 \cdot ZH_2O$, wherein M is a univalent or bivalent metal ion such as sodium or calcium, n is the valence of this metal ion and X is a coefficient of this metal ion, Y is a coefficient of the silica, and Z is the number of water crystallized. For the zeolite employed in the method of this invention, the metal ion M is exchangeable with the antibacterial metal ions, such as silver ions, copper ions or zinc ions, whereby the antibacterial metal ions are retained in the zeolite. Silver metal ions may be incorporated in the zeolite at 0.001 to 10% by weight (based on weight of anhydrous zeolite), more preferably 0.001 to 5%; zinc or copper ions may be incorporated at 0.01 to 25% by weight, more preferably 0.01 to 15% by weight. Antibacterial zeolites are known in the art and can be prepared by known methods, such as disclosed in U.S. Pat. No. 4,525,410, the disclosure of which is incorporated herein by reference.

Another inorganic carrier which can retain antibacterial metal ions is an amorphous aluminosilicate. Such materials have an amorphous three-dimensional skeleton and may be represented by the formula $XM_{2/n}O \cdot Al_2O_3 \cdot YSiO_2$ wherein the variables are defined as above for the zeolite. Silver metal ions may be incorporated in the carrier at 0.001 to 20% by weight (based on a dry weight of the carrier), more preferably 0.001 to 12%; zinc or copper ions may be incorporated at 0.01 to 15% by weight, more preferably 0.01 to 10% by weight. Antibacterial amorphous aluminosilicates are known in the art and can be prepared by known methods, such as disclosed in U.S. Pat. No. 4,959,268, the disclosure of which is incorporated herein by reference.

The inorganic carrier retaining antibacterial metal ions can be incorporated in the resin by known methods. For example, the inorganic carrier can be provided in particulate form and the resin can be provided as polymer chips, and these two materials can be blended together. Subsequently, the final blended material can be molded into an article by conventional molding methods, such as injection molding or blow molding.

The amount of the inorganic carrier incorporated in the resin is selected to provide the desired release of the antibacterial metal ions. Factors influencing this selection include the amount of antibacterial metal ions retained in the carrier and the ability of these metal ions to leach from the resin to the solution in contact therewith. Higher amounts of zeolite can be employed where a higher or faster release of antibacterial metal ions is desired. Additionally, it has been found that for the above-described zeolites, the antibacterial metal ions leach more slowly from polypropylene than high density polyethylene. Accordingly, a particular resin can be selected to meet desired release characteristics as can be readily determined by a person of ordinary skill in the art.

Generally, it is preferred that the inorganic carrier retaining the metal ions is incorporated in the resin at 0.01 to 30% by weight of the resin, with 0.5 to 10% being more preferred.

The following examples further illustrate preferred embodiments of the present invention.

EXAMPLE 1

Preparation of Bottles Containing Antibacterial Zeolite

A zeolite containing 3.5% silver ions and 6.5% zinc ions (Bactekiller AZ ™ from Kanebo Zeolite USA, Inc.) was blended into high density polyethylene (HDPE) (Marlex HDPE 5502 BN ™, Phillips Chemical Co.) or polypropylene (PPro) (Dypro 7231S PP ™, Fina Oil and Chemical Co.) at 10% by weight to obtain HDPE and PPro master chips. The HDPE and PPro master chips were blended with untreated HDPE and PPro, respectively, at concentrations of 2% and 4.5% by weight along with titanium oxide colorant. The final polymer chips were blow molded into 1-ounce oval bottles.

Control bottles were molded from HDPE without any antibacterial zeolite.

EXAMPLE 2

Preparation of Contact Lens Cases Containing Antibacterial Zeolite

The zeolite from Example 1 was blended into low density polyethylene (LDPE) (Rexene 20-40

LDPE TM, Rexene Plastics) at 10% by weight to obtain LDPE master chips. The LDPE master chips were blended with titanium oxide colorant and untreated LDPE at concentrations of 2% and 4.5% by weight. The final polymer chips were molded into contact lens cases each including two cells and a sealable cap for the cells.

Control contact lens cases were molded from LDPE without any antibacterial zeolite.

EXAMPLE 3

Antibacterial Efficacy Test

To determine antibacterial efficacy of the bottles prepared in Example 1, 0.85% sterile, unpreserved saline solution and a preserved conditioning solution for rigid gas permeable contact lenses (preserved with edetate disodium at 0.05% and chlorhexidine gluconate at 0.006%) were placed in the bottles from Example 1 and the bottles were capped. Six days later, the solutions were inoculated with adapted Serratia marcescens 48 at-a concentration of $1.8 \times 10^6$ cfu/ml. Bacterial counts taken at days following inoculation are reported in Tables 1 and 2. Each of the sample bottles in Table 1 contained the conditioning solution (CS), and each of the sample bottles in Table 2 contained the saline solution (SS). In the tables, ND indicates "not determined".

TABLE 1

| CS Sample | 1 Day | 2 Days |
|---|---|---|
| HDPE w/o Zeolite | $3.0 \times 10^1$ | <10 |
| HDPE w/ 4.5% Zeo | <10 | <10 |
| HDPE w/ 2.0% Zeo | <10 | <10 |
| PPro w/ 4.5% Zeo | <10 | <10 |
| PPro w/ 2.0% Zeo | $3.0 \times 10^1$ | <10 |

TABLE 2

| SS Sample | 1 Day | 2 Days | 3 Days | 5 Days | 14 Days |
|---|---|---|---|---|---|
| HDPE w/o Zeolite | $>5.0 \times 10^4$ | $>5.0 \times 10^4$ | ND | ND | $>5.0 \times 10^4$ |
| HDPE w/4.5% Zeo | $1.3 \times 10^4$ | $3.0 \times 10^3$ | $8.6 \times 10^2$ | $7.0 \times 10^1$ | $1.1 \times 10^2$ |
| HDPE w/2.0% Zeo | $>5.0 \times 10^4$ | $4.7 \times 10^3$ | $8.7 \times 10^2$ | $3.5 \times 10^2$ | $4.0 \times 10^1$ |
| PPro W/4.5% Zeo | $>5.0 \times 10^4$ | $>5.0 \times 10^4$ | $3.8 \times 10^3$ | $2.0 \times 10^1$ | <10 |
| PPro w/2.0% Zeo | $>5.0 \times 10^4$ | $>5.0 \times 10^4$ | $>5.0 \times 10^4$ | $>5.0 \times 10^4$ | $>5.0 \times 10^4$ |

The HDPTE bottles composed of a resin containing antibacterial zeolite, and the PPro bottles composed of a resin containing the zeolite at 4.5%, decreased the viability of the bacteria in comparison with the control bottles composed of a resin containing no antibacterial zeolites. The lower efficacy of the PPro bottles composed of the resin containing the zeolite at 2% is attributed to low levels of metal ions leached from the resins, as the metal ions leached more slowly from polypropylene than from HDPE.

EXAMPLE 4

Antibacterial Efficacy Test

To determine antibacterial efficacy of the lens cases prepared in Example 2, 1-ml samples of the above preserved conditioning solution, contaminated with $2.0 \times 10^7$ cfu of adapted Serratia marcescens 48, were placed in each cell of the lens cases. A lens case molded from LDPE, which contained no antibacterial zeolite, was used as the control, and the same amount of contaminated conditioning solution was employed in the control lens case. The data are reported in Table 3.

TABLE 3

| Lens Case | 1 Day |
|---|---|
| LDPE w/o Zeolite | $5.0 \times 10^4$ |
| LDPE w/2.0% Zeo | <10 |
| LDPE w/4.5% Zeo | <10 |

The lens cases composed of a resin containing the antibacterial zeolite provided almost complete eradication of the bacteria after one day.

The following tests in Examples 5 to 7 were conducted to simulate more closely the potential effects of a lens case becoming contaminated during a contact lens care regimen.

EXAMPLE 5

Antibacterial Efficacy Test

The cells of lens cases molded from LDPE were initially filled with 1-ml samples of the above preserved conditioning solution. The control lens case contained no antibacterial zeolite. After one day, the conditioning solution was replaced with 1-ml of fresh conditioning solution. This regimen was followed for three consecutive days. On the next day, the conditioning solution was removed from the cells, the cells were inoculated with a 0.01-ml saline suspension of microorganisms, and 1-ml of conditioning solution was added to the cells contaminated with the microorganisms. The suspension contained Pseudomonas cepacia (PC) at $4.4-10^5$ cfu/$\mu$l, Staphylococcus aureus (SA) at $1.6 \times 10^6$ cfu/$\mu$l and adapted S. marcescens 48 (SM) at $1.5 \times 10^6$ cfu/$\mu$l. After the inoculation, the solutions were sampled at various times. The data reported in Table 4 is based on time after inoculation. TNTC indicates too numerous to count.

TABLE 4

| Lens Case | Organism | 5 Hrs | 1 Day | 3 Days |
|---|---|---|---|---|
| LDPE w/o Zeolite | PC | $228 \times 10^3$ | TNTC | TNTC |
|  | SA | $111 \times 10^3$ | $9 \times 10^1$ | $0 \times 10^1$ |
|  | SM | $988 \times 10^3$ | TNTC | TNTC |
| LDPE w/ 2.0% Zeo | PC | $25 \times 10^3$ | $0 \times 10^1$ | $0 \times 10^1$ |
|  | SA | $95 \times 10^1$ | $0 \times 10^1$ | $0 \times 10^1$ |
|  | SM | $400 \times 10^3$ | $180 \times 10^1$ | $0 \times 10^1$ |
| LDPE w/ 4.5% Zeo | PC | $6 \times 10^1$ | $0 \times 10^1$ | $3 \times 10^1$ |
|  | SA | $3 \times 10^1$ | $0 \times 10^1$ | $0 \times 10^1$ |
|  | SM | $262 \times 10^3$ | $0 \times 10^1$ | $0 \times 10^1$ |

The data indicated that the lens cases molded from resins containing antibacterial zeolite enhanced antibacterial efficacy of the contact lens conditioning solution.

EXAMPLE 6

Antibacterial Efficacy Test

The cells of a series of lens cases molded from LDPE were initially filled with 1-ml samples of a preserved conditioning solution for rigid gas permeable contact lenses (preserved with edetate disodium at 0.05% and polyhexamethylene biguanide at 0.0015%), and each cell was inoculated with a 0.1-ml solution containing adapted *S. marcescens* 27 at $1.1 \times 10^7$ cfu. Microorganisms were enumerated from various cells at intervals of 6 hours, 1 day and 3 days following inoculation, as reported in Table 5. Additionally, for the cells used for the 1-day and 3-day time points, following enumeration of floating (planktonic) bacteria, the solution was removed from the cell and replaced with a nutrient broth (Letheen Broth); if any surviving organisms adhered to the surface of the cells, the nutrient broth would allow them to propagate relatively quickly. In Table 5, "+" indicates the presence of adhered microorganisms on surfaces of the cell, and "−" indicates no adhered microorganisms.

The data demonstrated that in contrast to the control lens cases, the cases containing antibacterial zeolite enhanced efficacy of the preserved solution by retarding growth of microorganisms on the surfaces of the lens case cells and inhibiting adherence of microorganisms to the surfaces.

TABLE 5

| Lens Case | 6 Hrs Planktonic | 1 Day Planktonic | 1 Day Adhered* | 3 Days Plantonic | 3 Days Adhered* |
|---|---|---|---|---|---|
| LDPE w/o Zeolite | $0 \times 10^1$ | $0 \times 10^1$ | + | $0 \times 10^1$ | + |
| LDPE w/2.0% Zeo | $0 \times 10^1$ | $0 \times 10^1$ | − | $0 \times 10^1$ | − |
| LDPE w/4.5% Zeo | $0 \times 10^1$ | $0 \times 10^1$ | − | $0 \times 10^1$ | − |

*Three days in nutrient broth following planktonic count.

EXAMPLE 7

Antibacterial Efficacy Test

The cells of lens cases molded from LDPE were inoculated with a 0.1-ml sample containing *S. marcescens* 27 ($1.2 \times 10^5$ cfu). After one hour, the samples were removed, and the lens cases were rinsed twice with saline solution. Then, 1-ml of tryptic soy broth (1 g/l) was added to each well, and the solution was aspirated with a pipet to mix. A 0.1-ml aliquot was removed at the intervals in Table 6, and the microorganisms in the samples were enumerated at each interval.

TABLE 6

| Lens Case | 0 Hour | 1 Hour | 6 Hours | 24 Hours |
|---|---|---|---|---|
| LDPE w/o Zeolite | $1 \times 10^1$ | $1 \times 10^1$ | $760 \times 10^1$ | TNTC |
| LDPE w/o Zeolite (Prosil coated)* | $9 \times 10^1$ | $28 \times 10^1$ | $1780 \times 10^1$ | TNTC |
| LDPE w/ 2.0% Zeo | $5 \times 10^1$ | $0 \times 10^1$ | $0 \times 10^1$ | $0 \times 10^1$ |
| LDPE w/ 4.5% Zeo | $1 \times 10^1$ | $0 \times 10^1$ | $0 \times 10^1$ | $0 \times 10^1$ |

*Lens case coated with Prosil-28, an organosilane surface treating agent for rendering a surface hydrophobic.

The data indicated that the lens cases molded from resins containing antibacterial zeolite protected the container from contamination by reducing bacterial adherence to the surfaces and killing viable microorganisms. In contrast, microorganisms propagated quickly in the lens cases lacking the zeolite.

While certain preferred embodiments have been described, it is understood that the invention is not limited thereto and modifications and variations would be evident to a person of ordinary skill in the art.

We claim:

1. A method for improving the antibacterial efficacy of an ophthalmic solution comprising:
   providing an article molded from a plastic resin including antibacterial metal ions in an inorganic carrier; and
   placing the ophthalmic solution in contact with said article, whereby said antibacterial metal ions leach into said ophthalmic solution.

2. The method of claim 1, wherein said metal ions are selected from the group consisting of silver ions, copper ions, zinc ions and combinations thereof.

3. The method of claim 2, wherein said inorganic carrier is selected from the group consisting of a zeolite and an amorphous aluminosilicate.

4. The method of claim 1, wherein said resin includes a zeolite carrier retaining silver ions.

5. The method of claim 4, wherein said zeolite carrier is present at 0.01 to 20% by weight of the resin.

6. The method of claim 1, wherein the article is a contact lens solution dispensing bottle or a portion thereof in contact with said solution.

7. In a contact lens case comprising at least one cell including a cavity adapted to store a contact lens and an ophthalmic solution therein, and a sealable cover for said cavity, the improvement wherein the cell is molded from a resin including antibacterial metal ions in an inorganic carrier, wherein said antibacterial metal ion is leachable from said resin to an ophthalmic solution stored in said cell.

8. The contact lens case of claim 7, wherein said metal ions are selected from the group consisting of silver ions, copper ions, zinc ions and combinations thereof.

9. The contact lens case of claim 8, wherein said inorganic carrier is selected from the group consisting of a zeolite and an amorphous aluminosilicate.

10. The contact lens case of claim 1, wherein said resin includes a zeolite carrier retaining silver ions.

11. The contact lens case of claim 10, wherein said zeolite carrier is present at 0.01 to 20% by weight of the resin.

12. A combination comprising:
   a container for storing an ophthalmic solution molded from a resin including antibacterial metal ions in an inorganic carrier; and
   an ophthalmic solution contained in said container, wherein said antibacterial metal ions are leachable from said resin to said ophthalmic solution.

13. The combination of claim 12, wherein said metal ions are selected from the group consisting of silver ions, copper ions, zinc ions and combinations thereof.

14. The combination of claim 13, wherein said inorganic carrier is selected from the group consisting of a zeolite and an amorphous aluminosilicate.

15. The combination of claim 1, wherein said resin includes a zeolite carrier retaining silver ions.

16. The combination of claim 15, wherein said zeolite carrier is present at 0.01 to 20% by weight of the resin.

17. The combination of claim 12, wherein said container is a contact lens solution dispensing bottle.

18. The combination of claim 12, wherein said container is a contact lens case.

19. A combination comprising:
a container for storing an ophthalmic solution;
an ophthalmic solution contained in said container; and
a substrate molded from a resin including antibacterial metal ions in an inorganic carrier in contact with said ophthalmic solution in said container,
wherein said antibacterial metal ions are leachable from said resin to said ophthalmic solution.

20. The combination of claim 19, wherein said container is a contact lens solution dispensing bottle.

* * * * *